United States Patent
Hammer (10) Patent No.: US 9,726,199 B2
(45) Date of Patent: Aug. 8, 2017

(54) AIR FRESHENING SYSTEM AND METHOD

(71) Applicant: Scott David Hammer, Dallas, TX (US)

(72) Inventor: Scott David Hammer, Dallas, TX (US)

( * ) Notice: Subject to any disclaimer, the term of this patent is extended or adjusted under 35 U.S.C. 154(b) by 537 days.

(21) Appl. No.: 13/843,078

(22) Filed: Mar. 15, 2013

(65) Prior Publication Data

US 2014/0271130 A1    Sep. 18, 2014

(51) Int. Cl.
| | | |
|---|---|---|
| F04D 29/70 | (2006.01) | |
| A61L 9/12 | (2006.01) | |
| F04D 19/00 | (2006.01) | |
| A61L 9/04 | (2006.01) | |

(52) U.S. Cl.
CPC ............ F04D 29/703 (2013.01); A61L 9/122 (2013.01); F04D 19/002 (2013.01); F04D 29/705 (2013.01); *A61L 9/042* (2013.01); *Y10T 29/49826* (2015.01)

(58) Field of Classification Search
CPC .... F04D 29/701; F04D 29/703; F04D 29/705; F04D 29/70; A61L 9/042
See application file for complete search history.

(56) References Cited

U.S. PATENT DOCUMENTS

| | | |
|---|---|---|
| 5,240,653 A | 8/1993 | Ramkissoon |
| 5,662,835 A | 9/1997 | Collingwood |
| 5,947,815 A | 9/1999 | Danforth |
| 6,878,057 B1 | 4/2005 | Calloura |
| 7,007,863 B2 | 3/2006 | Kotary et al. |
| 7,670,401 B2 * | 3/2010 | Whittemore .................... 55/480 |
| 8,746,587 B2 | 6/2014 | Soldan et al. |
| 2005/0169813 A1* | 8/2005 | D'Amico et al. ............ 422/124 |
| 2010/0038443 A1 | 2/2010 | Pankhurst et al. |
| 2010/0054920 A1* | 3/2010 | Xu .......................... F04D 29/70 415/121.2 |
| 2010/0078498 A1 | 4/2010 | Gasper |
| 2010/0116898 A1 | 5/2010 | Litten-Brown et al. |
| 2010/0163639 A1 | 7/2010 | Pankhurst et al. |
| 2010/0187324 A1 | 7/2010 | Feygin et al. |
| 2010/0237162 A1 | 9/2010 | Litten-Brown et al. |
| 2010/0294852 A1 | 11/2010 | Banco et al. |
| 2011/0204158 A1 | 8/2011 | Saari |
| 2011/0303757 A1 | 12/2011 | Blondeau et al. |
| 2012/0024974 A1 | 2/2012 | Grodsky et al. |
| 2012/0024975 A1 | 2/2012 | Sharma et al. |
| 2012/0079945 A1* | 4/2012 | Roberts ......................... 96/222 |
| 2012/0126024 A1 | 5/2012 | Boyd et al. |

OTHER PUBLICATIONS

Felix Buccellato et al., "What Ever Marketer Should Know about Fragrance," Oct. 2, 2001, pp. 1-8.

* cited by examiner

*Primary Examiner* — Bryan Lettman
(74) *Attorney, Agent, or Firm* — D. Scott Hemingway; Hemingway & Hansen, LLP (57) ABSTRACT

An airflow fan accessory comprising an accessory having a scented fabric and a fastening mechanism located along the outer edge of the scented fabric. In a preferred embodiment, the accessory may be easily attached to and detached from the fan blade enclosure of any typical airflow fan. Upon air flow through the fan and airflow fan accessory, a pleasant scent may be imparted to the room via release of scent from the scented fabric component.

21 Claims, 5 Drawing Sheets

AIR FRESHENING SYSTEM AND METHOD

RELATED APPLICATION DATA

Not applicable.

TECHNICAL FIELD

The present invention relates in general to a system and method for providing an accessory for an air fan such as a stand-alone box, round, and/or oscillating fan.

BACKGROUND OF THE INVENTION

Airflow fans allow the flow of heated or cooled air into rooms of homes, offices, other buildings and even outside. Generally, such fans are made of metal and/or plastic with a cage or enclosure like structure surrounding the spinning fan blades. They may have a switch or dial which can regulate the spinning speed of the fan blades which, in turn, regulates the amount of air which flows through the fan. Various stand alone fans appear in the market including box, round, and/or oscillating fans.

Various devices have been used in the past to scent the air of a given room or area in a building. However, such devices may require electricity or heat in order to volatilize the scent so that it distributes throughout the area of interest. The problem with prior art systems is the inability to conceivably, effectively, and easily access the airflow passing through the airflow fans to scent the air in the room.

SUMMARY OF THE INVENTION

The present invention supports an airflow fan accessory comprising an airflow fan accessory comprising an accessory having a scented fabric and a fastening mechanism located along the outer edge of the scented fabric. In a preferred embodiment, the accessory may be easily attached to and detached from the fan blade enclosure of any typical airflow fan. Upon air flow through the fan and airflow fan accessory, a pleasant scent may be imparted to the room via release of scent from the scented fabric component.

The fastening mechanisms may include elastic bands, straps, hooks, clips, and various other fastening means. The airflow fan accessory is easily removed when the fragrance has diminished and another airflow fan accessory is installed.

DETAILED DESCRIPTION

A system providing an airflow fan accessory is herein disclosed. The airflow fan accessory comprises a scented fabric and a fastening mechanism for attaching the scented fabric to a fan.

Figure 1:
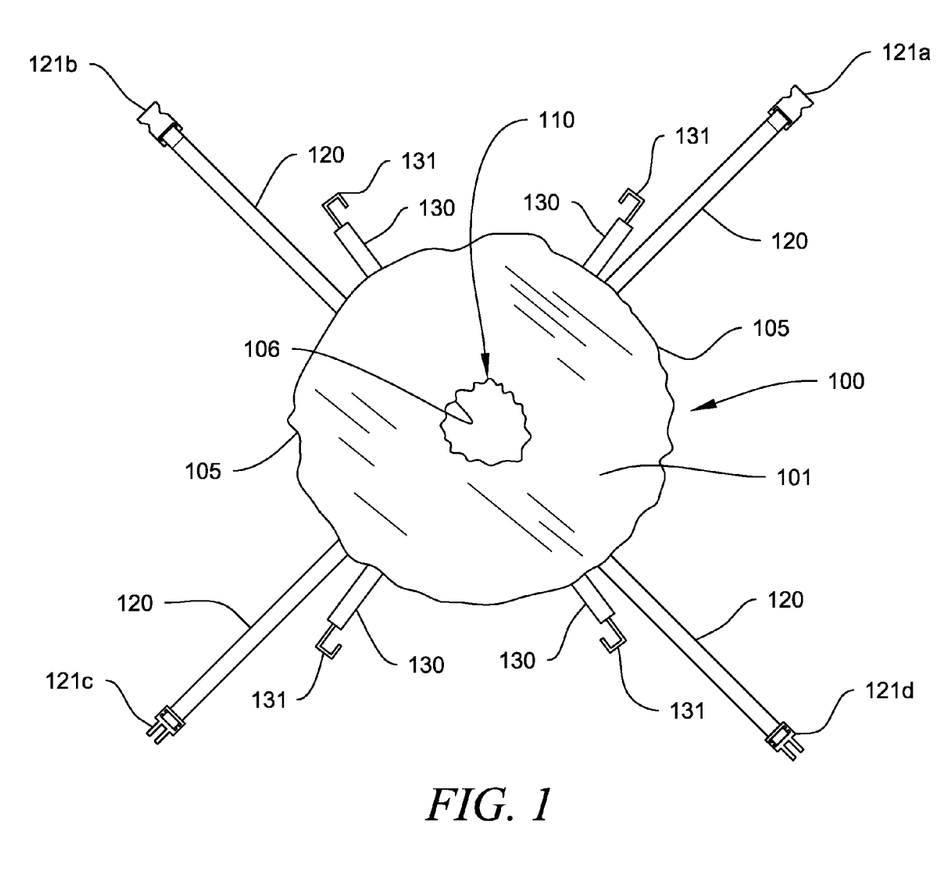
FIG. 1 is a front view illustrating an embodiment of an airflow fan accessory in accordance with the principles of the present invention.

The airflow fan accessory 100 comprises a scented material and various fastening mechanisms. FIG. 1 illustrates an embodiment of the airflow fan accessory 100. A scented fabric 101 is used for the scenting material. The embodiment shown in FIG. 1 is intended for a round fan. The scented fabric 101 is preferably a bunch of loosely gathered material with a holding band 105 secured along the outer edge of the scented fabric 101.

The holding band 105 is preferably a circular elastic band with enough elasticity to expand big enough to at least fit around the large circumference of a fan blade enclosure. When placing the scented fabric 101 onto the fan blade enclosure, the user stretches the holding band 105 out and places it around the fan blade enclosure. As the holding band 105 is stretched out, the loosely gathered material of the scented fabric becomes more taught. The scented fabric 101 with holding band 105 act cooperatively similar to a common shower cap.

The scented fabric 101 may also define a hole 110. An inner band 106 may be secured along the edge of hole 110. This is beneficial if the motor axle enclosure of the fan extends forward past the front side of the fan blade enclosure. Inner band 106 is preferably a circular elastic band with enough elasticity to expand big enough to at least fit around the extended motor axle enclosure. The inner band 106 may be expanded by the user or by the scented fabric 101 as it becomes taut.

Figure 6:
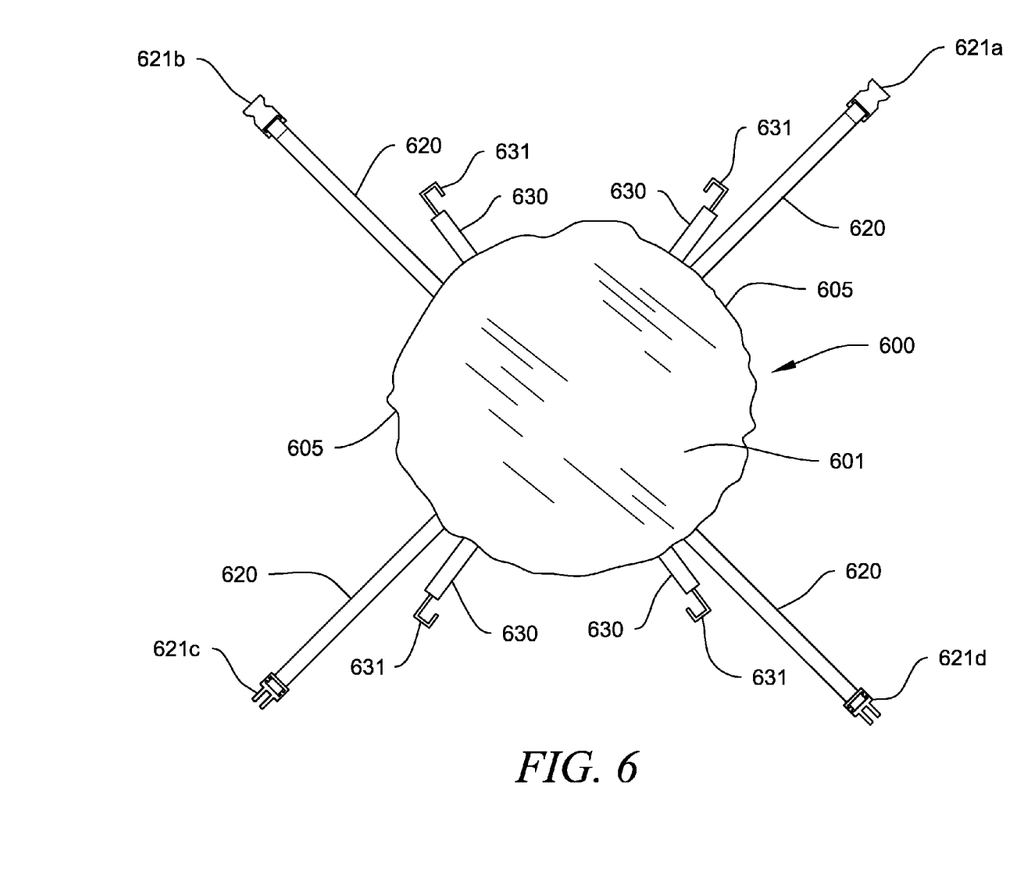
FIG. 6 is a front view illustrating an alternate embodiment of an airflow fan accessory in accordance with the principles of the present invention.

Alternatively, scented fabric 101 may not define a hole 110 (see FIG. 6). Scented fabric 101 may also define perforation that allows a user to remove the middle area of the scented fabric 101 to create said hole 110. Inner band 106 may or may not be used with the alternative embodiment.

The airflow fan accessory 100 may also comprise other fastening mechanisms. Straps 120 may be used to provide the scented fabric 101 with stability and additional securement. In this embodiment, four straps are used, but any number of straps may be used that to help stabilize and secure the scented fabric 101. One end of each of the four straps is secured to the outer edge of the scented fabric 101.

The other end of each strap is secured to a clip or connector (121a, 121b, 121c and 121d). The straps 120 are wrapped around the back side of the fan blade enclosure and attached to another connector. Each connector may be attached to any of the other non-attached connectors. Preferably connector 121a is attached to connector 121c and connector 121b attached to connector 121d as this provides the best stability and securement (shown in FIG. 4 in further detail).

Additionally, the outer edge of scented fabric 101 may comprise connectors secured thereto to which connectors (121a, 121b, 121c and 121d) may be attached. Each strap 120 may also comprise an adjuster that allows the user to lengthen or shorten the strap. The adjusters will allow the straps to remain taut despite where the strap is connected similar to a shoulder strap adjuster on a bra.

The straps may be made of various materials including nylon strands, thin rope, elastic strands, or any other material that can maintain a tension when in use. The connectors can be clips, hooks and loops, snaps, buttons, or any other fasteners common to the fastening art. Double-sided adhesive may also be used to attach the accessory to the fan.

In addition to or in place of the straps 120, fastening hooks 131 may be employed. The fastening hooks 131 are secured to one end of the hook straps 130. The opposite end of the hook straps 130 is secured to the outer edge of the scented fabric 101. Preferably the hook straps 130 are an elastic material to allow easy extension of said hook strap 130 and instant tension once hook 131 is fastened. The hooks 131 are preferably structured to hook around the fan blade enclosure bars (shown in FIGS. 2-4 in further detail).

Preferably, the scented fabric comprises a substrate which may be made of natural fibers, synthetic fibers, or a mixture of natural fiber and synthetic fibers. Exemplary natural fibers that can be used to form the substrate include wood fibers and non-wood natural fibers such as vegetable fibers, cotton, straw, canes, silk, animal fiber, grasses, hemp, and corn stalks.

Nonwoven fabrics for use with FIG. 1 are broadly defined as sheet or web structures bonded together by entangling fiber or filaments (and by perforating films) mechanically, thermally or chemically. They are typically flat, porous sheets that are made directly from separate fibers or from molten plastic or plastic film. Some examples of nonwoven materials are staple nonwovens, spun laid nonwovens, and air-laid paper. Woven fabric is a cloth formed by weaving. Synthetic fibers may include a variety of substrates known in the art. An exemplary fiber is polylactide fiber or PLA. PLA is a biodegradable thermoplastic derived from lactic acid.

The fabric material has a weight of approximately 0.2 to 2.0 oz/ft$^2$, but can have weights that vary from 0.05 to 4.55 oz/ft$^2$. An exemplary combination substrate for the fabric comprises a mixture of 0.1 wt. % to 1.00 wt. % of the polylactide fiber and about 10 wt. % to about 1.00 wt. % of the natural fiber. The fabric preferably is flame retardant, and can be composed of a polyester or natural material (woven or non-woven). The airflow rate should be extremely high on the order a thin mesh that freely allows airflow. The fabric component has a high degree of air permeability on the order of not impeding airflow by more than 5% to 10% by uncovered air flow rates.

The scented fabric component is preferably thin, but must be sturdy enough to withstand typical ventilation flows of fan systems without being torn or compromised such that it cannot perform the intended function. The ventilation rate is normally expressed by the volumetric flow rate of air flow. The typical units used are cubic feet per minute (CFM) or liters per second (L/s). The ventilation rate can also be expressed on a per person or per unit floor area basis, such as CFM/p or CFM/ft$^2$.

For residential housing, which mostly relies on air infiltration for ventilation, the common ventilation rate measure is the number of times the whole interior volume of air is replaced per hour, and is called air changes per hour (I or ACH; units of 1/h). During the winter, ACH may range from 0.50 to 0.41 in a tightly insulated house to 1.11 to 1.47 in a loosely insulated house.

The scenting fabric has an air freshening agent loaded thereon. The air freshening agent must be able to adhere to the fabric but at least a portion thereof should be released when air flows through the scented fabric component. In the natural operation of the fan system, air will flow through the scenting material.

Thus the air freshening agent may be chosen to release when air of any temperature flows through the scenting material at a pre-determined rate. Sufficient air freshening agent should continue to adhere to the scenting fabric so that the air freshening accessory can provide air freshening benefits for a pre-determined period of time. After the pre-determined period of time, it is contemplated that the airflow fan accessory will be replaced.

Figure 2:
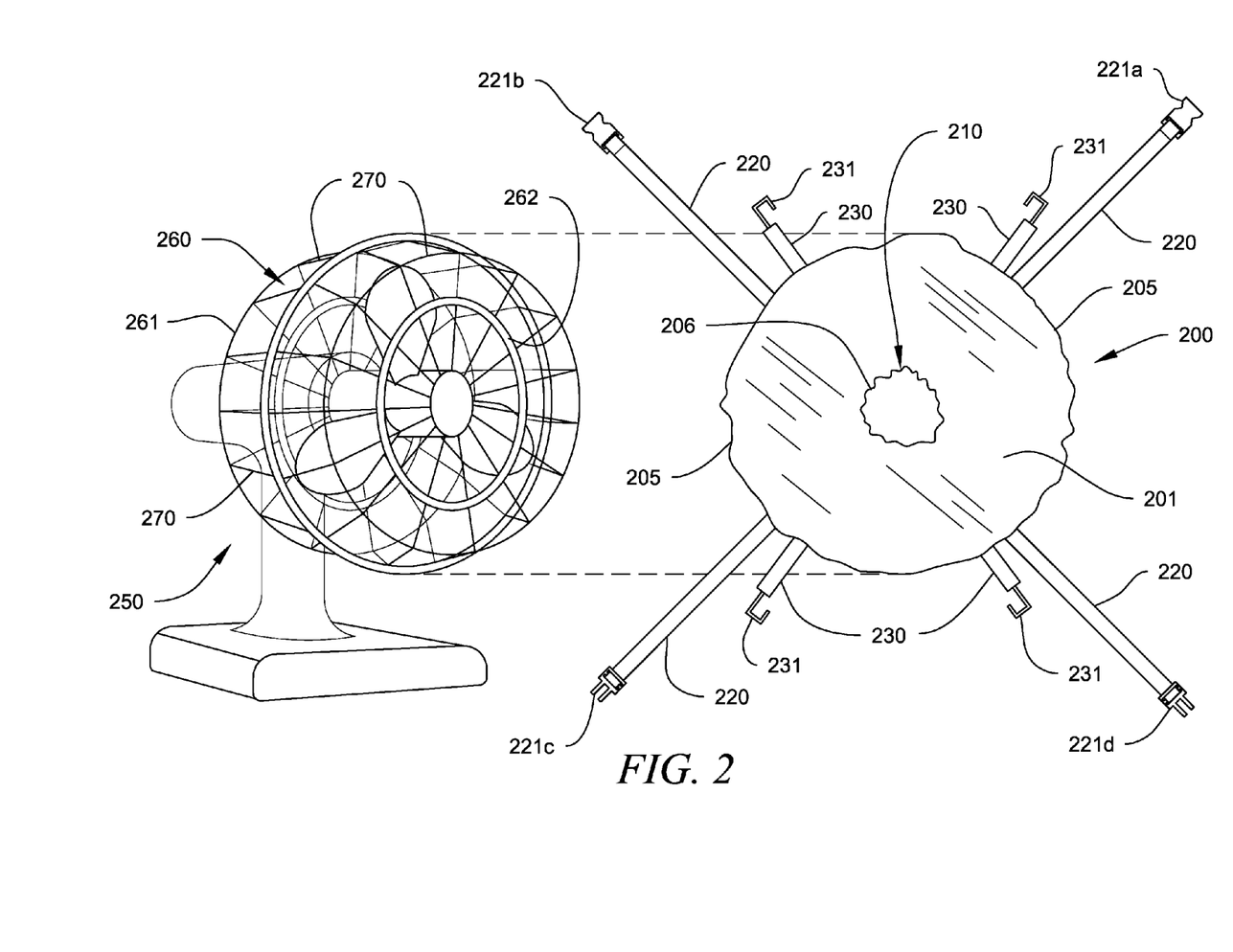
FIG. 2 is an assembly perspective environmental view illustrating an embodiment of an airflow register accessory in accordance with the principles of the present invention installed on a round airflow fan.

Referring to FIG. 2, the accessory 200 further comprises a scenting material. FIG. 2 illustrates a scented fabric 201 used for the scenting material. FIG. 2 illustrates an embodiment of the airflow fan accessory 200. A scented fabric 201 is used for the scenting material. The embodiment shown in FIG. 2 is intended for a round shaped fan enclosure. A common round fan 250 comprises a base, a motor, fan blades, and a fan blade enclosure 260. The fan blade enclosure 260 has a back side 261 and a front side 262. The airflow through the fan goes in through the back side 261 and out through the front side 262. The fan blade enclosure 260 typically comprises bars 270 that run laterally and longitudinally to form the fan blade enclosure structure. The bars 270 of the fan blade enclosure 260 are typically made of any rigid material, most commonly a metal or plastic.

The scented fabric 201 is preferably a bunch of loosely gathered material with a holding band 205 secured along the outer edge of the scented fabric 201. The holding band 205 is preferably a circular elastic band with enough elasticity to expand big enough to at least fit around the large circumference of a fan blade enclosure. When placing the scented fabric 201 onto the fan blade enclosure 260, the user stretches the holding band 205 out and places it around the fan blade enclosure 260 with the scented fabric adjacent the front side 262 of fan blade enclosure 260.

As the holding band 205 is stretched out, the loosely gathered material of the scented fabric becomes more taught. Once placed on the enclosure, some of the scented fabric 201 may extend past the front side 262 and lie adjacent the back side 261 of fan blade enclosure 260. When the holding band 205 is released by user after surrounding the front side 262 with the scented fabric 201, the elasticity of the holding band 205 tightens itself onto the fan blade enclosure. The scented fabric 201 with holding band 205 act cooperatively similar to a common shower cap.

The scented fabric 201 may also define a hole 210. An inner band 206 may be secured along the edge of hole 210. This is beneficial if the motor axle enclosure of the fan extends forward past the front side 262 of fan blade enclosure 260. Inner band 206 is preferably a circular elastic band with enough elasticity to expand big enough to at least fit around the extended motor axle enclosure. The inner band 206 may be expanded by the user or by the scented fabric 201 as it becomes taut.

Alternatively, scented fabric 201 may not define a hole 210 (see FIG. 6). Scented fabric 201 may also define perforation that allows a user to remove the middle area of the scented fabric 201 to create said hole 210. Inner band 206 may or may not be used with the alternative embodiment.

The airflow fan accessory 200 may also comprise other fastening mechanisms. Straps 220 may be used to provide the scented fabric 201 with stability and additional securement. In this embodiment, four straps are used, but any number of straps may be used that to help stabilize and secure the scented fabric 201. One end of each of the four straps is secured to the outer edge of the scented fabric 201. The other end of each strap is secured to a clip or connector (221*a*, 221*b*, 221*c* and 221*d*).

The straps 220 are wrapped around the back side 261 of the fan blade enclosure 260 and attached to another connector. Each connector may be attached to any of the other non-attached connectors. Preferably connector 221a is attached to connector 221c and connector 221b attached to connector 221d as this provides the best stability and securement (shown in FIG. 4 in further detail). Straps 220 help the scented fabric 201 maintain its position on the fan blade enclosure 260 by deterring its removal from outside forces such as airflow from the fan.

Additionally, the outer edge of scented fabric 201 may comprise connectors secured thereto to which connectors (221a, 221b, 221c and 221d) may be attached. Each strap 220 may also comprise an adjuster that allows the user to lengthen or shorten the strap. The adjusters will allow the straps to remain taut despite where the strap is connected similar to a shoulder strap adjuster on a bra.

The straps may be made of various materials including nylon strands, thin rope, elastic strands, or any other material that can maintain a tension when in use. The connectors can be clips, hooks and loops, snaps, buttons, or any other fasteners common to the fastening art. Double-sided adhesive may also be used to attach the accessory to the fan.

In addition to or in place of the straps 220, fastening hooks 231 may be employed. The fastening hooks 231 are secured to one end of the hook straps 230. The opposite end of the hook straps 230 is secured to the outer edge of the scented fabric 201. Preferably the hook straps 230 are an elastic material to allow easy extension of said hook strap 230 and instant tension once hook 231 is fastened. The hooks 231 are preferably structured to hook around the fan blade enclosure bars 270.

As most fans have multiple bars 270 extending the perimeter of the enclosure both laterally and longitudinally, the hooks 231 have various fastening points the user may choose from. Similar to the straps 220, the hooks 231 and hook straps 230 help the scented fabric 201 maintain its position on the fan blade enclosure 260 by deterring its removal from outside forces such as airflow from the fan. Straps 220 and hook straps 230 may be used in conjunction or separate. Different embodiments may employ both methods, one of the methods, or neither.

Alternatively, the scented fabric 201 substantially surrounds the entire fan blade enclosure 260. In this alternative embodiment, the holding band 205 preferably has a resting size approximate the perimeter of the motor that is secured to the back side 261 of the fan blade enclosure 260. That would allow the scented fabric to substantially surround the fan blade enclosure 260 with the elasticity of the holding band 205 helping the scented fabric 201 maintain its position on the fan blade enclosure 260 by deterring its removal from outside forces such as airflow from the fan.

Preferably, the scented fabric comprises a substrate which may be made of natural fibers, synthetic fibers, or a mixture of natural fiber and synthetic fibers. Exemplary natural fibers that can be used to form the substrate include wood fibers and non-wood natural fibers such as vegetable fibers, cotton, straw, canes, silk, animal fiber, grasses, hemp, and corn stalks.

Nonwoven fabrics for use with FIG. 2 are broadly defined as sheet or web structures bonded together by entangling fiber or filaments (and by perforating films) mechanically, thermally or chemically. They are typically flat, porous sheets that are made directly from separate fibers or from molten plastic or plastic film. Some examples of nonwoven materials are staple nonwovens, spun laid nonwovens, and air-laid paper. Woven fabric is a cloth formed by weaving. Synthetic fibers may include a variety of substrates known in the art. An exemplary fiber is polylactide fiber or PLA. PLA is a biodegradable thermoplastic derived from lactic acid.

The fabric material has a weight of approximately 0.2 to 2.0 oz/ft$^2$, but can have weights that vary from 0.05 to 4.55 oz/ft$^2$. An exemplary combination substrate for the fabric comprises a mixture of 0.1 wt. % to 1.00 wt. % of the polylactide fiber and about 10 wt. % to about 1.00 wt. % of the natural fiber. The fabric preferably is flame retardant, and can be composed of a polyester or natural material (woven or non-woven). The airflow rate should be extremely high on the order a thin mesh that freely allows airflow. The fabric component has a high degree of air permeability on the order of not impeding airflow by more than 5% to 10% by uncovered air flow rates.

The scented fabric component is preferably thin, but must be sturdy enough to withstand typical ventilation flows of fan systems without being torn or compromised such that it cannot perform the intended function. The typical units used are cubic feet per minute (CFM) or liters per second (L/s). The ventilation rate can also be expressed on a per person or per unit floor area basis, such as CFM/p or CFM/ft$^2$.

For residential housing, which mostly relies on air infiltration for ventilation, the common ventilation rate measure is the number of times the whole interior volume of air is replaced per hour, and is called air changes per hour (I or ACH; units of 1/h). During the winter, ACH may range from 0.50 to 0.41 in a tightly insulated house to 1.11 to 1.47 in a loosely insulated house.

The scenting fabric has an air freshening agent loaded thereon. The air freshening agent must be able to adhere to the fabric but at least a portion thereof should be released when air flows through the scented fabric component. In the natural operation of the fan system, air will flow through the scenting material. Thus the air freshening agent may be chosen to release when air of any temperature flows through the scenting material at a pre-determined rate. Sufficient air freshening agent should continue to adhere to the scenting fabric so that the air freshening accessory can provide air freshening benefits for a pre-determined period of time. After the pre-determined period of time, it is contemplated that the airflow fan accessory will be replaced.

Figure 3:
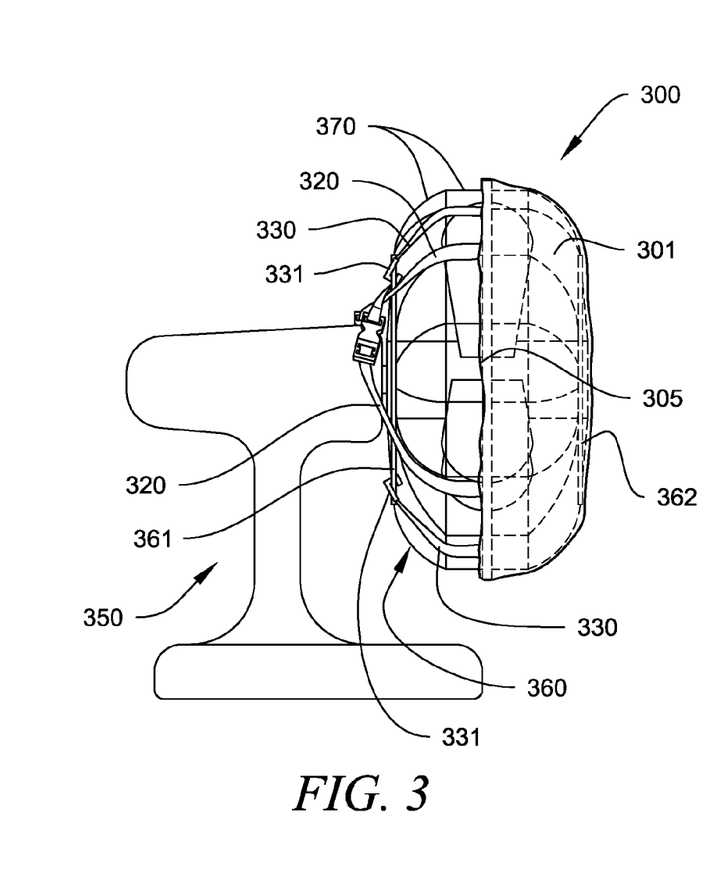
FIG. 3 is a side view illustrating an embodiment of an airflow fan accessory installed on a round airflow fan.

Referring to FIG. 3, the accessory 300 further comprises a scenting material. FIG. 3 illustrates a scented fabric 301 used for the scenting material. FIG. 3 illustrates a side view of an embodiment of the airflow fan accessory 300. A scented fabric 301 is used for the scenting material. The embodiment shown in FIG. 3 is intended for a round shaped fan enclosure. A common round fan 350 comprises a base, a motor, fan blades, and a fan blade enclosure 360.

The fan blade enclosure 360 has a back side 361 and a front side 362. The airflow through the fan goes in through the back side 361 and out through the front side 362. The fan blade enclosure 360 typically comprises bars 370 that run laterally and longitudinally to form the fan blade enclosure structure. The bars 370 of the fan blade enclosure 360 are typically made of any rigid material, most commonly a metal or plastic.

The scented fabric 301 is preferably a bunch of loosely gathered material with a holding band 305 secured along the outer edge of the scented fabric 301. The holding band 305 is preferably a circular elastic band with enough elasticity to expand big enough to at least fit around the large circumference of a fan blade enclosure. When placing the scented fabric 301 onto the fan blade enclosure 360, the user stretches the holding band 305 out and places it around the fan blade enclosure 360 with the scented fabric adjacent the front side 362 of fan blade enclosure 360.

As the holding band 305 is stretched out, the loosely gathered material of the scented fabric becomes more taught. Once placed on the enclosure, some of the scented fabric 301 may extend past the front side 362 and lie adjacent the back side 361 of fan blade enclosure 360. When the holding band 305 is released by user after surrounding the front side 362 with the scented fabric 301, the elasticity of the holding band 305 tightens itself onto the fan blade enclosure. The scented fabric 301 with holding band 305 act cooperatively similar to a common shower cap.

The scented fabric 301 may also define a hole (not visible). An inner band (not visible) may be secured along the edge of the hole. This is beneficial if the motor axle enclosure of the fan extends forward past the front side 362 of fan blade enclosure 360. The inner band is preferably a circular elastic band with enough elasticity to expand big enough to at least fit around the extended motor axle enclosure. The inner band may be expanded by the user or by the scented fabric 101 as it becomes taut.

Alternatively, scented fabric 301 may not define a hole (see FIG. 6). Scented fabric 301 may also define perforation that allows a user to remove the middle area of the scented fabric 301 to create said hole. The inner band may or may not be used with the alternative embodiment.

The airflow fan accessory 300 may also comprise other fastening mechanisms. Straps 320 may be used to provide the scented fabric 301 with stability and additional securement. In this embodiment, four straps are used, but any number of straps may be used that to help stabilize and secure the scented fabric 301. One end of each of the four straps is secured to the outer edge of the scented fabric 301. The other end of each strap is secured to a clip or connector. The straps 320 are wrapped around the back side 361 of the fan blade enclosure 360 and attached to another connector. Each connector may be attached to any of the other non-attached connectors. Straps 320 help the scented fabric 301 maintain its position on the fan blade enclosure 360 by deterring its removal from outside forces such as airflow from the fan.

Additionally, the outer edge of scented fabric 301 may comprise connectors secured thereto to which the strap connectors may be attached. Each strap 320 may also comprise an adjuster that allows the user to lengthen or shorten the strap. The adjusters will allow the straps to remain taut despite where the strap is connected similar to a shoulder strap adjuster on a bra.

The straps may be made of various materials including nylon strands, thin rope, elastic strands, or any other material that can maintain a tension when in use. The connectors can be clips, hooks and loops, snaps, buttons, or any other fasteners common to the fastening art. Double-sided adhesive may also be used to attach the accessory to the fan.

In addition to or in place of the straps 320, fastening hooks 331 may be employed. The fastening hooks 331 are secured to one end of the hook straps 330. The opposite end of the hook straps 330 is secured to the outer edge of the scented fabric 301. Preferably the hook straps 330 are an elastic material to allow easy extension of said hook strap 330 and instant tension once hook 331 is fastened. The hooks 331 are preferably structured to hook around the fan blade enclosure bars 370. As most fans have multiple bars 370 extending the perimeter of the enclosure both laterally and longitudinally, the hooks 331 have various fastening points the user may choose from.

Similar to the straps 320, the hooks 331 and hook straps 330 help the scented fabric 301 maintain its position on the fan blade enclosure 360 by deterring its removal from outside forces such as airflow from the fan. Straps 320 and hook straps 330 may be used in conjunction or separate. Different embodiments may employ both methods, one of the methods, or neither.

Alternatively, the scented fabric 301 substantially surrounds the entire fan blade enclosure 360. In this alternative embodiment, the holding band 305 preferably has a resting size approximate the perimeter of the motor that is secured to the back side 361 of the fan blade enclosure 360. That would allow the scented fabric to substantially surround the fan blade enclosure 360 with the elasticity of the holding band 305 helping the scented fabric 301 maintain its position on the fan blade enclosure 360 by deterring its removal from outside forces such as airflow from the fan.

Preferably, the scented fabric comprises a substrate which may be made of natural fibers, synthetic fibers, or a mixture of natural fiber and synthetic fibers. Exemplary natural fibers that can be used to form the substrate include wood fibers and non-wood natural fibers such as vegetable fibers, cotton, straw, canes, silk, animal fiber, grasses, hemp, and corn stalks.

Nonwoven fabrics for use with FIG. 3 are broadly defined as sheet or web structures bonded together by entangling fiber or filaments (and by perforating films) mechanically, thermally or chemically. They are typically flat, porous sheets that are made directly from separate fibers or from molten plastic or plastic film. Some examples of nonwoven materials are staple nonwovens, spun laid nonwovens, and air-laid paper. Woven fabric is a cloth formed by weaving. Synthetic fibers may include a variety of substrates known in the art. An exemplary fiber is polylactide fiber or PLA. PLA is a biodegradable thermoplastic derived from lactic acid.

The fabric material has a weight of approximately 0.2 to 2.0 oz/ft$^2$, but can have weights that vary from 0.05 to 4.55 oz/ft$^2$. An exemplary combination substrate for the fabric comprises a mixture of 0.1 wt. % to 1.00 wt. % of the polylactide fiber and about 10 wt. % to about 1.00 wt. % of the natural fiber. The fabric preferably is flame retardant, and can be composed of a polyester or natural material (woven or non-woven). The airflow rate should be extremely high on the order a thin mesh that freely allows airflow. The fabric component has a high degree of air permeability on the order of not impeding airflow by more than 5% to 10% by uncovered air flow rates.

The scented fabric component is preferably thin, but must be sturdy enough to withstand typical ventilation flows of fan systems without being torn or compromised such that it cannot perform the intended function. The typical units used are cubic feet per minute (CFM) or liters per second (L/s). The ventilation rate can also be expressed on a per person or per unit floor area basis, such as CFM/p or CFM/ft$^2$.

For residential housing, which mostly relies on air infiltration for ventilation, the common ventilation rate measure is the number of times the whole interior volume of air is replaced per hour, and is called air changes per hour (I or ACH; units of 1/h). During the winter, ACH may range from 0.50 to 0.41 in a tightly insulated house to 1.11 to 1.47 in a loosely insulated house.

The scenting fabric has an air freshening agent loaded thereon. The air freshening agent must be able to adhere to the fabric but at least a portion thereof should be released when air flows through the scented fabric component. In the natural operation of the fan system, air will flow through the scenting material. Thus the air freshening agent may be chosen to release when air of any temperature flows through the scenting material at a pre-determined rate.

Sufficient air freshening agent should continue to adhere to the scenting fabric so that the air freshening accessory can provide air freshening benefits for a pre-determined period of time. After the pre-determined period of time, it is contemplated that the airflow fan accessory will be replaced.

Figure 4:
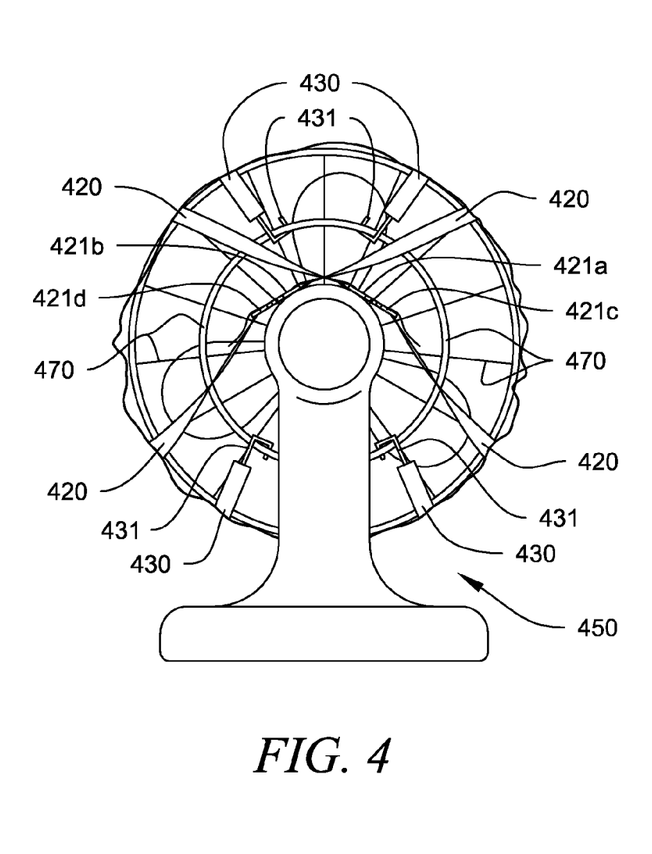
FIG. 4 is a back view illustrating an embodiment of an airflow fan accessory installed on a round airflow fan.

Referring to FIG. 4, the accessory 400 further comprises a scenting material. FIG. 4 illustrates a scented fabric 401 used for the scenting material. FIG. 4 illustrates a back view of an embodiment of the airflow fan accessory 400. A scented fabric 401 is used for the scenting material. The embodiment shown in FIG. 4 is intended for a round shaped fan enclosure. A common round fan 450 comprises a base, a motor, fan blades, and a fan blade enclosure 460.

The fan blade enclosure 460 has a back side 461 and a front side. The airflow through the fan goes in through the back side 461 and out through the front side 462. The fan blade enclosure 460 typically comprises bars 470 that run laterally and longitudinally to form the fan blade enclosure structure. The bars 470 of the fan blade enclosure 460 are typically made of any rigid material, most commonly a metal or plastic.

The scented fabric 401 may also define a hole (not visible). An inner band (not visible) may be secured along the edge of the hole. This is beneficial if the motor axle enclosure of the fan extends forward past the front side 462 of fan blade enclosure 460. The inner band is preferably a circular elastic band with enough elasticity to expand big enough to at least fit around the extended motor axle enclosure. The inner band may be expanded by the user or by the scented fabric 401 as it becomes taut.

Alternatively, scented fabric 401 may not define a hole (see FIG. 6). Scented fabric 401 may also define perforation that allows a user to remove the middle area of the scented fabric 401 to create said hole. The inner band may or may not be used with the alternative embodiment.

The scented fabric 401 is preferably a bunch of loosely gathered material with a holding band 405 secured along the outer edge of the scented fabric 401. The holding band 405 is preferably a circular elastic band with enough elasticity to expand big enough to at least fit around the large circumference of a fan blade enclosure. When placing the scented fabric 401 onto the fan blade enclosure 460, the user stretches the holding band 405 out and places it around the fan blade enclosure 460 with the scented fabric adjacent the front side 462 of fan blade enclosure 460.

As the holding band 405 is stretched out, the loosely gathered material of the scented fabric becomes more taught. Once placed on the enclosure, some of the scented fabric 401 may extend past the front side 462 and lie adjacent the back side 461 of fan blade enclosure 460. When the holding band 405 is released by user after surrounding the front side 462 with the scented fabric 401, the elasticity of the holding band 405 tightens itself onto the fan blade enclosure. The scented fabric 401 with holding band 405 act cooperatively similar to a common shower cap.

The airflow fan accessory 400 may also comprise other fastening mechanisms. Straps 420 may be used to provide the scented fabric 401 with stability and additional securement. In this embodiment, four straps are used, but any number of straps may be used that to help stabilize and secure the scented fabric 401. One end of each of the four straps is secured to the outer edge of the scented fabric 401. The other end of each strap is secured to a clip or connector (421a, 421b, 421c and 421d). The straps 420 are wrapped around the back side 461 of the fan blade enclosure 460 and attached to another connector.

Each connector may be attached to any of the other non-attached connectors. Preferably connector 421a is attached to connector 421c and connector 421b attached to connector 421d as this provides the best stability and securement (shown in FIG. 4 in further detail). Straps 420 help the scented fabric 401 maintain its position on the fan blade enclosure 460 by deterring its removal from outside forces such as airflow from the fan.

Additionally, the outer edge of scented fabric 401 may comprise connectors secured thereto to which connectors (421a, 421b, 421c and 421d) may be attached. Each strap 420 may also comprise an adjuster that allows the user to lengthen or shorten the strap. The adjusters will allow the straps to remain taut despite where the strap is connected similar to a shoulder strap adjuster on a bra.

The straps may be made of various materials including nylon strands, thin rope, elastic strands, or any other material that can maintain a tension when in use. The connectors can be clips, hooks and loops, snaps, buttons, or any other fasteners common to the fastening art. Double-sided adhesive may also be used to attach the accessory to the fan.

In addition to or in place of the straps 420, fastening hooks 431 may be employed. The fastening hooks 431 are secured to one end of the hook straps 430. The opposite end of the hook straps 430 is secured to the outer edge of the scented fabric 401. Preferably the hook straps 430 are an elastic material to allow easy extension of said hook strap 430 and instant tension once hook 431 is fastened. The hooks 431 are preferably structured to hook around the fan blade enclosure bars 470. As most fans have multiple bars 470 extending the perimeter of the enclosure both laterally and longitudinally, the hooks 431 have various fastening points the user may choose from.

Similar to the straps 420, the hooks 431 and hook straps 430 help the scented fabric 401 maintain its position on the fan blade enclosure 460 by deterring its removal from outside forces such as airflow from the fan. Straps 420 and hook straps 430 may be used in conjunction or separate. Different embodiments may employ both methods, one of the methods, or neither.

Alternatively, the scented fabric 401 substantially surrounds the entire fan blade enclosure 460. In this alternative embodiment, the holding band 405 preferably has a resting size approximate the perimeter of the motor that is secured to the back side 461 of the fan blade enclosure 460. That would allow the scented fabric to substantially surround the fan blade enclosure 460 with the elasticity of the holding band 405 helping the scented fabric 401 maintain its position on the fan blade enclosure 460 by deterring its removal from outside forces such as airflow from the fan.

Preferably, the scented fabric comprises a substrate which may be made of natural fibers, synthetic fibers, or a mixture of natural fiber and synthetic fibers. Exemplary natural fibers that can be used to form the substrate include wood fibers and non-wood natural fibers such as vegetable fibers, cotton, straw, canes, silk, animal fiber, grasses, hemp, and corn stalks. Nonwoven fabrics for use with FIG. 4 are broadly defined as sheet or web structures bonded together by entangling fiber or filaments (and by perforating films) mechanically, thermally or chemically.

They are typically flat, porous sheets that are made directly from separate fibers or from molten plastic or plastic film. Some examples of nonwoven materials are staple nonwovens, spun laid nonwovens, and air-laid paper. Woven fabric is a cloth formed by weaving. Synthetic fibers may include a variety of substrates known in the art. An exemplary fiber is polylactide fiber or PLA. PLA is a biodegradable thermoplastic derived from lactic acid.

The fabric material has a weight of approximately 0.2 to 2.0 oz/ft$^2$, but can have weights that vary from 0.05 to 4.55 oz/ft$^2$. An exemplary combination substrate for the fabric comprises a mixture of 0.1 wt. % to 1.00 wt. % of the polylactide fiber and about 10 wt. % to about 1.00 wt. % of the natural fiber. The fabric preferably is flame retardant, and can be composed of a polyester or natural material (woven or non-woven). The airflow rate should be extremely high on the order a thin mesh that freely allows airflow. The fabric component has a high degree of air permeability on the order of not impeding airflow by more than 5% to 10% by uncovered air flow rates.

The scented fabric component is preferably thin, but must be sturdy enough to withstand typical ventilation flows of fan systems without being torn or compromised such that it cannot perform the intended function. The typical units used are cubic feet per minute (CFM) or liters per second (L/s). The ventilation rate can also be expressed on a per person or per unit floor area basis, such as CFM/p or CFM/ft$^2$.

For residential housing, which mostly relies on air infiltration for ventilation, the common ventilation rate measure is the number of times the whole interior volume of air is replaced per hour, and is called air changes per hour (I or ACH; units of 1/h). During the winter, ACH may range from 0.50 to 0.41 in a tightly insulated house to 1.11 to 1.47 in a loosely insulated house.

The scenting fabric has an air freshening agent loaded thereon. The air freshening agent must be able to adhere to the fabric but at least a portion thereof should be released when air flows through the scented fabric component. In the natural operation of the fan system, air will flow through the scenting material. Thus the air freshening agent may be chosen to release when air of any temperature flows through the scenting material at a pre-determined rate. Sufficient air freshening agent should continue to adhere to the scenting fabric so that the air freshening accessory can provide air freshening benefits for a pre-determined period of time. After the pre-determined period of time, it is contemplated that the airflow fan accessory will be replaced.

Figure 5:
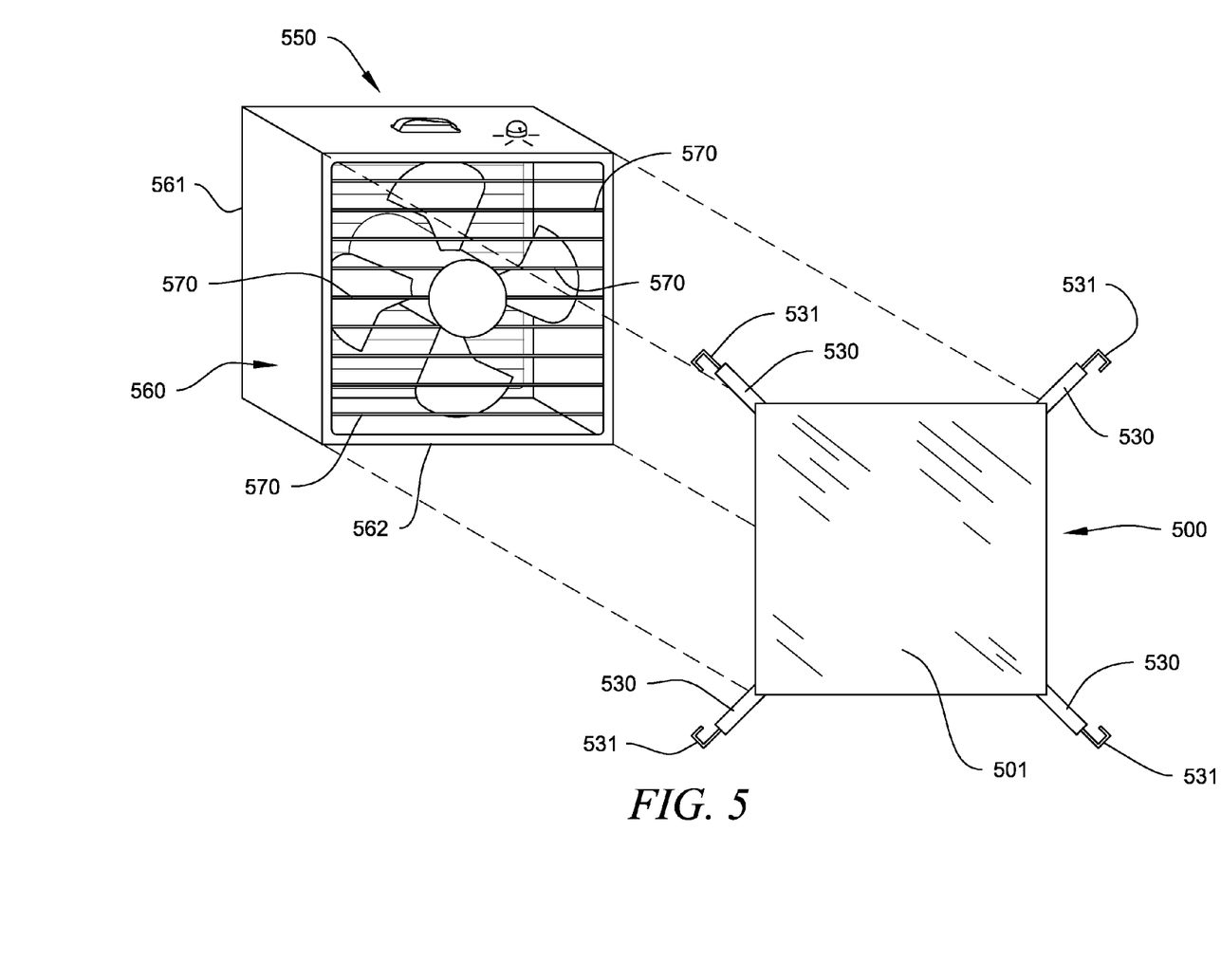
FIG. 5 is an assembly perspective environmental view illustrating an embodiment of an airflow register accessory in accordance with the principles of the present invention installed on a box airflow fan.

Referring to FIG. 5, the accessory 500 further comprises a scenting material. FIG. 5 illustrates a scented fabric 501 used for the scenting material. FIG. 5 illustrates an embodiment of the airflow fan accessory 500. A scented fabric 501 is used for the scenting material. The embodiment shown in FIG. 5 is intended for a box shaped fan enclosure.

A common box fan 550 comprises a base, a motor, fan blades, and a fan blade enclosure 560. The fan blade enclosure 560 has a back side 561 and a front side 562. The airflow through the fan goes in through the back side 561 and out through the front side 562. The fan blade enclosure 560 typically comprises bars 570 that run laterally and/or longitudinally to help form the fan blade enclosure structure. The bars 570 of the fan blade enclosure 560 are typically made of a rigid material, most commonly a metal or plastic.

The scented fabric 501 is preferably a sheet material. When placing the scented fabric 501 onto the fan blade enclosure 560, the user places the scented fabric 501 so that scented fabric 501 lies flat adjacent the front side 562 of fan blade enclosure 560. Once placed on the enclosure, some of the scented fabric 501 may extend past the front side 562 and lie adjacent the back side 561 of fan blade enclosure 560.

The airflow fan accessory 500 comprises fastening mechanisms. Fastening hooks 531 are secured to one end of the hook straps 530. The opposite end of the hook straps 530 is secured to the outer edge of the scented fabric 501. Preferably the hook straps 530 are an elastic material to allow easy extension of said hook strap 530 and instant tension once hook 531 is fastened. The hooks 531 are preferably structured to hook around the fan blade enclosure bars 570. The straps may be made of various materials including nylon strands, thin rope, elastic strands, or any other material that can maintain a tension when in use. Double-sided adhesive may also be used to attach the accessory to the fan.

As most fans have multiple bars 570 extending the perimeter of the enclosure both laterally and longitudinally, the hooks 531 have various fastening points the user may choose from. The hooks 531 and hook straps 530 help the scented fabric 501 maintain its position on the fan blade enclosure 560 by deterring its removal from outside forces such as airflow from the fan.

In addition to or in place of the hook straps 530, other straps may be employed. Other straps (not shown) may be used to provide the scented fabric with additional stability and securement. One end of each of the four straps is secured to the outer edge of the scented fabric. The other end of each strap is secured to a clip or connector. The straps are wrapped around the back side 561 of the fan blade enclosure 560 and attached to another connector. Each connector may be attached to any of the other non-attached connectors. The other straps can also help the scented fabric 501 maintain its position on the fan blade enclosure 560 by deterring its removal from outside forces such as airflow from the fan.

Additionally, the outer edge of scented fabric 501 may comprise connectors secured thereto to which the connectors on the other straps may be attached. Each strap may also comprise an adjuster that allows the user to lengthen or shorten the strap. The adjusters will allow the straps to remain taut despite where the strap is connected similar to a shoulder strap adjuster on a bra.

The straps may be made of various materials including nylon strands, thin rope, elastic strands, or any other material that can maintain a tension when in use. The connectors can be clips, hooks and loops, snaps, buttons, or any other fasteners common to the fastening art. Double-sided adhesive may also be used to attach the accessory to the fan. The hook straps 530 and other straps may be used in conjunction or separate. Different embodiments may employ both methods, one of the methods, or neither.

Alternatively, the scented fabric 501 acts like a sleeve. The scented fabric or scented sleeve would slide substantially around the entire fan blade enclosure 560. In this alternative embodiment, the scented fabric would lie adjacent the back side 561 and the front side 562 while also lying adjacent the sides. The advantages of this embodiment may be: an embodiment free of fastening mechanisms as the scented fabric would just slide on and around the fan blade enclosure; double scenting the airflow as both the intake and exhaust air would be scented; and longer lasting as the user could shift the sleeve position so that the portion of the scented fabric adjacent the enclosure sides shift to lie adjacent the front or back sides if the path of the airflow. As the scented fabric would be a single piece that surrounds the enclosure, it would not be removed from outside forces such as airflow from the fan.

Preferably, the scented fabric comprises a substrate which may be made of natural fibers, synthetic fibers, or a mixture of natural fiber and synthetic fibers. Exemplary natural fibers that can be used to form the substrate include wood fibers and non-wood natural fibers such as vegetable fibers, cotton, straw, canes, silk, animal fiber, grasses, hemp, and corn stalks.

Nonwoven fabrics for use with FIG. 5 are broadly defined as sheet or web structures bonded together by entangling fiber or filaments (and by perforating films) mechanically, thermally or chemically. They are typically flat, porous sheets that are made directly from separate fibers or from molten plastic or plastic film. Some examples of nonwoven materials are staple nonwovens, spun laid nonwovens, and air-laid paper. Woven fabric is a cloth formed by weaving. Synthetic fibers may include a variety of substrates known in the art. An exemplary fiber is polylactide fiber or PLA. PLA is a biodegradable thermoplastic derived from lactic acid.

The fabric material has a weight of approximately 0.2 to 2.0 oz/ft$^2$, but can have weights that vary from 0.05 to 4.55 oz/ft$^2$. An exemplary combination substrate for the fabric comprises a mixture of 0.1 wt. % to 1.00 wt. % of the polylactide fiber and about 10 wt. % to about 1.00 wt. % of the natural fiber. The fabric preferably is flame retardant, and can be composed of a polyester or natural material (woven or non-woven). The airflow rate should be extremely high on the order a thin mesh that freely allows airflow. The fabric component has a high degree of air permeability on the order of not impeding airflow by more than 5% to 10% by uncovered air flow rates.

The scented fabric component is preferably thin, but must be sturdy enough to withstand typical ventilation flows of fan systems without being torn or compromised such that it cannot perform the intended function. The typical units used are cubic feet per minute (CFM) or liters per second (L/s). The ventilation rate can also be expressed on a per person or per unit floor area basis, such as CFM/p or CFM/ft$^2$.

For residential housing, which mostly relies on air infiltration for ventilation, the common ventilation rate measure is the number of times the whole interior volume of air is replaced per hour, and is called air changes per hour (I or ACH; units of 1/h). During the winter, ACH may range from 0.50 to 0.41 in a tightly insulated house to 1.11 to 1.47 in a loosely insulated house.

The scenting fabric has an air freshening agent loaded thereon. The air freshening agent must be able to adhere to the fabric but at least a portion thereof should be released when air flows through the scented fabric component. In the natural operation of the fan system, air will flow through the scenting material. Thus the air freshening agent may be chosen to release when air of any temperature flows through the scenting material at a pre-determined rate. Sufficient air freshening agent should continue to adhere to the scenting fabric so that the air freshening accessory can provide air freshening benefits for a pre-determined period of time. After the pre-determined period of time, it is contemplated that the airflow fan accessory will be replaced.

The airflow fan accessory 600 comprises a scented material and various fastening mechanisms. FIG. 6 illustrates an embodiment of the airflow fan accessory 600. A scented fabric 601 is used for the scenting material. The embodiment shown in FIG. 6 is intended for a round fan. The scented fabric 601 is preferably a bunch of loosely gathered material with a holding band 605 secured along the outer edge of the scented fabric 601.

The holding band 605 is preferably a circular elastic band with enough elasticity to expand big enough to at least fit around the large circumference of a fan blade enclosure. When placing the scented fabric 601 onto the fan blade enclosure, the user stretches the holding band 605 out and places it around the fan blade enclosure. As the holding band 605 is stretched out, the loosely gathered material of the scented fabric becomes more taught. The scented fabric 601 with holding band 605 act cooperatively similar to a common shower cap. Unlike FIG. 1, FIG. 6 does not define a hole or comprise an inner band.

The airflow fan accessory 600 may also comprise other fastening mechanisms. Straps 620 may be used to provide the scented fabric 601 with stability and additional securement. In this embodiment, four straps are used, but any number of straps may be used that to help stabilize and secure the scented fabric 601. One end of each of the four straps is secured to the outer edge of the scented fabric 601. The other end of each strap is secured to a clip or connector (621a, 621b, 621c and 621d).

The straps 620 are wrapped around the back side of the fan blade enclosure and attached to another connector. Each connector may be attached to any of the other non-attached connectors. Preferably connector 621a is attached to connector 621c and connector 621b attached to connector 621d as this provides the best stability and securement (shown in FIG. 4 in further detail).

Additionally, the outer edge of scented fabric 601 may comprise connectors secured thereto to which connectors (621a, 621b, 621c and 621d) may be attached. Each strap 620 may also comprise an adjuster that allows the user to lengthen or shorten the strap. The adjusters will allow the straps to remain taut despite where the strap is connected similar to a shoulder strap adjuster on a bra.

The straps may be made of various materials including nylon strands, thin rope, elastic strands, or any other material that can maintain a tension when in use. The connectors can be clips, hooks and loops, snaps, buttons, or any other fasteners common to the fastening art. Double-sided adhesive may also be used to attach the accessory to the fan.

In addition to or in place of the straps 620, fastening hooks 631 may be employed. The fastening hooks 631 are secured to one end of the hook straps 630. The opposite end of the hook straps 630 is secured to the outer edge of the scented fabric 601. Preferably the hook straps 630 are an elastic material to allow easy extension of said hook strap 630 and instant tension once hook 631 is fastened. The hooks 631 are preferably structured to hook around the fan blade enclosure bars (shown in FIGS. 2-4 in further detail).

Preferably, the scented fabric comprises a substrate which may be made of natural fibers, synthetic fibers, or a mixture of natural fiber and synthetic fibers. Exemplary natural fibers that can be used to form the substrate include wood fibers and non-wood natural fibers such as vegetable fibers, cotton, straw, canes, silk, animal fiber, grasses, hemp, and corn stalks.

Nonwoven fabrics for use with FIG. 6 are broadly defined as sheet or web structures bonded together by entangling fiber or filaments (and by perforating films) mechanically, thermally or chemically. They are typically flat, porous sheets that are made directly from separate fibers or from molten plastic or plastic film. Some examples of nonwoven materials are staple nonwovens, spun laid nonwovens, and air-laid paper. Woven fabric is a cloth formed by weaving. Synthetic fibers may include a variety of substrates known in the art. An exemplary fiber is polylactide fiber or PLA. PLA is a biodegradable thermoplastic derived from lactic acid.

The fabric material has a weight of approximately 0.2 to 2.0 oz/ft$^2$, but can have weights that vary from 0.05 to 4.55 oz/ft$^2$. An exemplary combination substrate for the fabric comprises a mixture of 0.1 wt. % to 1.00 wt. % of the polylactide fiber and about 10 wt. % to about 1.00 wt. % of the natural fiber. The fabric preferably is flame retardant, and can be composed of a polyester or natural material (woven or non-woven). The airflow rate should be extremely high on the order a thin mesh that freely allows airflow. The fabric component has a high degree of air permeability on the order of not impeding airflow by more than 5% to 10% by uncovered air flow rates.

The scented fabric component is preferably thin, but must be sturdy enough to withstand typical ventilation flows of fan systems without being torn or compromised such that it cannot perform the intended function. The typical units used are cubic feet per minute (CFM) or liters per second (L/s). The ventilation rate can also be expressed on a per person or per unit floor area basis, such as CFM/p or CFM/ft$^2$.

For residential housing, which mostly relies on air infiltration for ventilation, the common ventilation rate measure is the number of times the whole interior volume of air is replaced per hour, and is called air changes per hour (I or ACH; units of 1/h). During the winter, ACH may range from 0.50 to 0.41 in a tightly insulated house to 1.11 to 1.47 in a loosely insulated house.

The scenting fabric has an air freshening agent loaded thereon. The air freshening agent must be able to adhere to the fabric but at least a portion thereof should be released when air flows through the scented fabric component. In the natural operation of the fan system, air will flow through the scenting material.

Thus the air freshening agent may be chosen to release when air of any temperature flows through the scenting material at a pre-determined rate. Sufficient air freshening agent should continue to adhere to the scenting fabric so that the air freshening accessory can provide air freshening benefits for a pre-determined period of time. After the pre-determined period of time, it is contemplated that the airflow fan accessory will be replaced.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

I claim:

1. An airflow accessory, comprising:
   an accessory fabric body with a flat fabric substrate having an outer surface, an inner surface, and being air permeable so as to allow an air flow to be channeled therethrough, said accessory fabric body being placed across a front surface of an exterior fan enclosure of a fan assembly, said accessory fabric body being stretched over said front surface of said exterior fan enclosure and adjusted to conform to the shape and size of said front surface of said exterior fan enclosure, said accessory fabric body having a circular perforated perimeter in a central area of the accessory fabric body to accommodate removal of fabric substrate inside said circular perforated perimeter of said accessory fabric body to reduce a coverage of said accessory fabric body said front surface of said exterior fan enclosure;
   a fastening mechanism having four hook straps and four securing straps,
      said four hook straps include a first hook strap, a second hook strap, a third hook strap and a fourth hook strap with each hook strap having one end of said hook strap coupled to the accessory fabric body and a hook located on an opposite end of each of said hook straps, said hook being configured to be attached to a rear of the exterior fan enclosure, said hook straps being positioned to assist in making the accessory fabric structure conform to the exterior shape and size of the front surface of the exterior fan enclosure;
   said four securing straps include a first securing strap, a second securing strap, a third securing strap and a fourth securing strap with each securing strap being coupled to said accessory fabric body on one end and having a buckle clip located on an other end of each securing strap, said first securing strap being an adjustable length elastic connector strap coupled to the accessory fabric body structure on a first end and having a first clip to secure a second end of said first securing strap to a fourth end of said second securing strap; said second securing strap being an adjustable length elastic connector strap coupled to the accessory fabric body structure on a third end and having a second clip to secure said fourth end of said second securing strap to said second end of said first securing strap; said third securing strap being an adjustable length elastic connector strap coupled to the accessory fabric body structure on a fifth end and having a third clip to secure a sixth end of said third securing strap to an eighth end of said fourth securing strap; and said fourth securing strap being an adjustable length elastic connector strap coupled to the accessory fabric body structure on a seventh end and having a fourth clip to secure said eighth end of said fourth securing strap to said sixth end of said third securing strap; said first, second, third, and fourth securing straps assisting in making the accessory fabric body conform to the exterior size and shape of said exterior fan enclosure, and,
   said accessory fabric body structure having a scented surface impregnated with a fragrance across said flat fabric substrate, said fragrance being emitted into the air flow channeled through the accessory fabric body structure.

2. The airflow accessory of claim 1, wherein said accessory fabric body structure is shaped to fit a round fan.

3. The airflow accessory of claim 1, wherein said accessory fabric body structure further comprises an elastic holding band on an outer perimeter of said accessory fabric body structure.

4. The airflow accessory of claim 1, wherein said accessory fabric body structure is shaped to fit a box fan.

5. The airflow accessory of claim 1, wherein said accessory body structure comprises scented strips impregnated with said fragrance.

6. The airflow accessory of claim 5, wherein said scented strips are made of a scented fabric.

7. The airflow accessory of claim 1, wherein said fragrance impregnated in said accessory fabric body structure comprises a scented gel.

8. An airflow accessory, comprising:
   an accessory fabric body having a flat fabric substrate with an outer surface and an inner surface, being air permeable so as to allow an air flow to be channeled therethrough, said accessory fabric body being placed across front and side surfaces of a fan assembly to conform to a shape thereof,
   a fastening mechanism having four hook straps and four securing straps,
      said four hook straps include a first hook strap, a second hook strap, a third hook strap, and a fourth hook strap with each hook strap having one end coupled to the accessory fabric body and an opposite end of each hook strap having a hook being attached to a rear portion of the fan assembly, each of said four hook straps being positioned to make the accessory fabric body conform to the shape and size of the fan assembly;

said four securing straps include a first securing strap, a second securing strap, a third securing strap, and a fourth securing strap, said first securing strap and said second securing strap coupled to said accessory fabric body on one end of each of said first and second securing straps and coupled to each other by a first reciprocal buckle clip assembly on their respective other ends, and said third securing strap and fourth securing straps coupled to said accessory fabric body on one end of each of said third and fourth securing straps and coupled to each other by a second reciprocal buckle clip assembly on their respective other ends, said securing straps assisting said accessory fabric body to conform to the shape and size of said fan assembly;

said accessory fabric body structure having a scented surface impregnated with a fragrance across the surface of said flat fabric substrate, said fragrance being emitted into the air flow channeled through the assembly body structure.

9. The airflow accessory of claim 8, wherein said accessory fabric body structure is shaped to fit a round fan.

10. The airflow accessory of claim 8, wherein said accessory fabric body structure further comprises an elastic holding band on an outer perimeter of said accessory fabric body structure.

11. The airflow accessory of claim 8, wherein said accessory fabric body structure is shaped to fit a box fan.

12. The airflow accessory of claim 8, wherein said accessory body structure comprises scented strips impregnated with said fragrance.

13. The airflow accessory of claim 12, wherein said scented strips are made of a scented fabric.

14. The airflow accessory of claim 8, wherein said fragrance impregnated in said accessory fabric body structure comprises a scented gel.

15. A method of providing a fabric substrate having air flow channeled therethrough secured to a fan enclosure, comprising the steps of:
  providing an accessory fabric body that is air permeable, has a flat fabric substrate, an outer surface, and an inner surface;
  configuring said accessory fabric body to be of a similar shape as a shape of said fan enclosure;
  providing a circular perforation perimeter in a central area of the accessory fabric body to accommodate removal of a portion of said accessory fabric body surrounded by said circular perforation to reduce a coverage of said accessory fabric body over a front surface of said fan enclosure;
  placing said accessory fabric body on an exterior surface of the fan enclosure of a fan assembly through the use of a fastening mechanism having four hook straps and four securing straps,
    said four hook straps including a first hook strap, a second hook strap, a third hook strap and a fourth hook strap coupled on one end of each of said hook straps to the accessory fabric body and having a hook on an opposite end of each of said hook straps being configured to be attached to a rear portion of the fan enclosure, said four hook straps being positioned to assist the accessory fabric body conform to a shape of the exterior surface of the fan enclosure;
    said four securing straps including a first securing strap, a second securing strap, a third securing strap and a fourth securing strap, said accessory fabric body being fastened with said securing straps to conform to the shape of said fan enclosure; said first securing strap being an adjustable length elastic connector strap coupled to the accessory fabric body on a first end and having a first clip securing a second end of said first securing strap to said second securing strap, said second securing strap being an adjustable length elastic connector strap coupled to the accessory fabric body on a third end and having a second clip securing a fourth end of said second securing strap to said second end of said first securing strap, said third securing strap being an adjustable length elastic connector strap coupled to the accessory fabric body on a fifth end and having a third clip securing a sixth end of said third securing strap to said fourth securing strap and said fourth strap being an adjustable length elastic connector strap coupled to the accessory fabric body on a seventh end and having a fourth clip securing an eighth end of said fourth securing strap to said sixth end of said third securing strap,
  locating one or more scented fragrances across the surface of said accessory fabric body, and
  emitting said one or more scented fragrances into the air flow channeled through the fan enclosure and the accessory fabric body.

16. The method of claim 15, wherein said accessory fabric body structure is shaped to fit a round fan.

17. The method of claim 15, wherein said accessory fabric body structure further comprises an elastic holding band on said outer perimeter of said accessory fabric body structure.

18. The method of claim 15, wherein said accessory fabric body structure is shaped to fit a box fan.

19. The method of claim 15, wherein said scented strips impregnated with said one or more scented fragrances are made of non-woven fabric.

20. The method of claim 15, wherein said scented strips impregnated with said one or more scented fragrances are made of woven fabric.

21. The method of claim 15, wherein said one or more scented fragrances impregnated in said scented strips comprises a scented gel.

* * * * *